United States Patent
Lambrecht et al.

[11] Patent Number: 6,036,696
[45] Date of Patent: Mar. 14, 2000

[54] GUIDE-PIN PLACEMENT DEVICE AND METHOD OF USE

[75] Inventors: Greg Lambrecht, Wyckoff, N.J.; Brett Jason Stern, New York, N.Y.; Jacob Einhorn, Washington, D.C.; Kathleen Nydzik Robbins, Brooklyn, N.Y.

[73] Assignee: Stryker Technologies Corporation, Kalamazoo, Mich.

[21] Appl. No.: 08/994,507

[22] Filed: Dec. 19, 1997

[51] Int. Cl.⁷ ................................................ A61B 17/17
[52] U.S. Cl. ............................................ 606/97; 606/104
[58] Field of Search ................................ 606/96, 97, 98, 606/104, 129, 130

[56] References Cited

U.S. PATENT DOCUMENTS

| | | |
|---|---|---|
| 2,200,120 | 5/1940 | Nauth . |
| 2,531,734 | 11/1950 | Hopkins . |
| 3,577,160 | 5/1971 | White . |
| 3,704,707 | 12/1972 | Halloran . |
| 3,867,932 | 2/1975 | Huene . |
| 3,991,310 | 11/1976 | Morrison . |
| 4,037,592 | 7/1977 | Kronner . |
| 4,418,422 | 11/1983 | Richter et al. . |
| 4,625,718 | 12/1986 | Olerud et al. . |
| 4,686,972 | 8/1987 | Kurland . |
| 4,722,336 | 2/1988 | Kim et al. . |
| 4,731,808 | 3/1988 | Ogunsunlade . |
| 4,803,976 | 2/1989 | Frigg et al. . |
| 4,848,327 | 7/1989 | Perdue . |
| 4,850,344 | 7/1989 | Olerud et al. . |
| 4,881,535 | 11/1989 | Sohngen . |
| 4,917,111 | 4/1990 | Pennig et al. . |
| 4,969,889 | 11/1990 | Greig . |
| 4,976,713 | 12/1990 | Landanger et al. . |
| 5,013,317 | 5/1991 | Cole et al. . |
| 5,031,203 | 7/1991 | Trecha . |
| 5,070,861 | 12/1991 | Einars et al. . |
| 5,112,336 | 5/1992 | Krevolin et al. . |
| 5,176,681 | 1/1993 | Lawes et al. . |
| 5,239,569 | 8/1993 | Saleh et al. . |
| 5,264,216 | 11/1993 | Bombardelli et al. . |
| 5,283,808 | 2/1994 | Cramer et al. . |
| 5,334,192 | 8/1994 | Behrens . |
| 5,426,687 | 6/1995 | Goodall et al. . |
| 5,478,343 | 12/1995 | Ritter . |
| 5,513,240 | 4/1996 | Hausmann et al. . |
| 5,584,838 | 12/1996 | Rona et al. . |
| 5,661,775 | 8/1997 | Cramer et al. . |

FOREIGN PATENT DOCUMENTS

| | | |
|---|---|---|
| 964149 | 11/1975 | Canada . |
| 0 755 660 A2 | 1/1997 | European Pat. Off. . |
| 0 428 452 A1 | 11/1990 | France . |
| 0 281 763 A2 | 2/1988 | Germany . |
| 0 405 132 A1 | 5/1990 | Germany . |
| 0 496 950 A1 | 10/1991 | Germany . |
| 32 05 404 A1 | 9/1993 | Germany . |
| 1323095 A1 | 7/1987 | U.S.S.R. . |

OTHER PUBLICATIONS

K.H. Pridie: "Intracapsular Fractures Of The Neck Of The Femur"; Jul. 17, 1937; The Lancet pp. 126–127.

*Primary Examiner*—Michael Buiz
*Assistant Examiner*—David O. Reip
*Attorney, Agent, or Firm*—Pennie & Edmonds LLP

[57] ABSTRACT

A hand instrument and method for use by a surgeon to target the appropriate entry point and trajectory on bony tissue through which an instrument, such as a nail, pin, screw, rod, wire, drill bit, or other implant is passed. Imbedded within the instrument is at least one relatively radio-opaque target which allows the user to predict with the use of an x-ray or fluoroscopic imaging device the placement of said instrument or implant before drilling it into place with the use of an x-ray or fluoroscopic imaging device. By manipulating the device around the axis of the guide piece, the surgeon can predict the placement of the instrument or implant without iterative insertion and removal of the instrument or implant itself.

6 Claims, 8 Drawing Sheets

GUIDE-PIN PLACEMENT DEVICE AND METHOD OF USE

BACKGROUND OF THE INVENTION

1. Field of the Invention

The present invention relates to a method and device to determine the alignment for the insertion of an instrument such as a pin, rod, nail, screw, wire, drill bit, or other implant into bony tissue using x-ray or fluoroscopy or the like to stabilize fractures or other bony tissue defects. More particularly, the method and device is designed for use by a surgeon to properly determine the point and trajectory of insertion of said instrument into a particular bone mass using an x-ray or fluoroscopic imaging device without the need to otherwise make multiple attempts to properly insert the instrument, such as a nail, pin, rod, screw, wire, drill bit, or other implant into the bony tissue.

2. Description of the Prior Art

Every year, in the United States and worldwide, large numbers of surgical procedures are performed in which an instrument, such as a nail, pin, rod, screw, wire, drill bit, or other implant is inserted into a bony tissue mass to stabilize a fracture or defect in such bony tissue mass. The nail or screw strengthens the bone and holds the parts of the bone together. For example, such a technique is used to fix a hip fracture. Hip fracture fixation with either compression hip screws (CHS) or intramedullary interlocking nails is one of the most common orthopedic surgical procedures. The surgeon's goals are accurate reduction and stabilization of the fracture until bony union occurs. For purposes of illustration herein, examples regarding the insertion of a pin into the proximal femur of a person will be referred to. This should in no way be interpreted as a limitation on the scope of this invention. Rather, the present invention includes, without limitation, devices used for insertion of instruments, such as pins, screws, rods, nails, wires, drill bits, or other implants into any bony tissue of a person or animal.

Figure 2A:
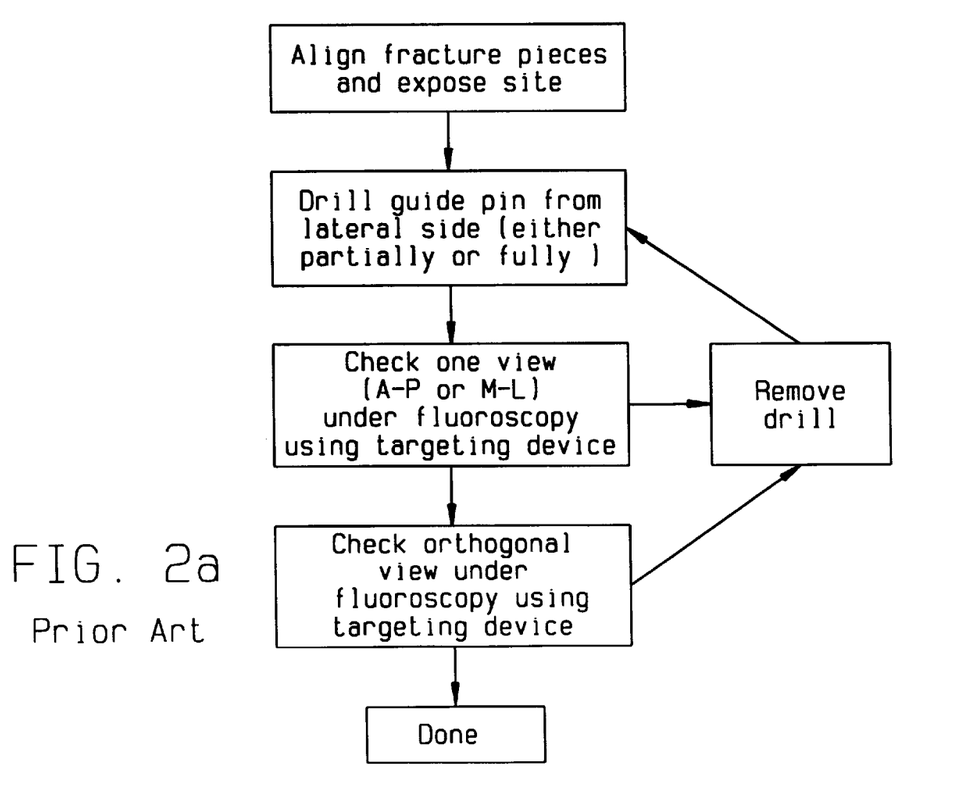
FIG. 2a is a flow chart depicting the current process a surgeon uses to properly insert a guide-pin across a femoral neck fracture into the femoral head.
Figure 2B:
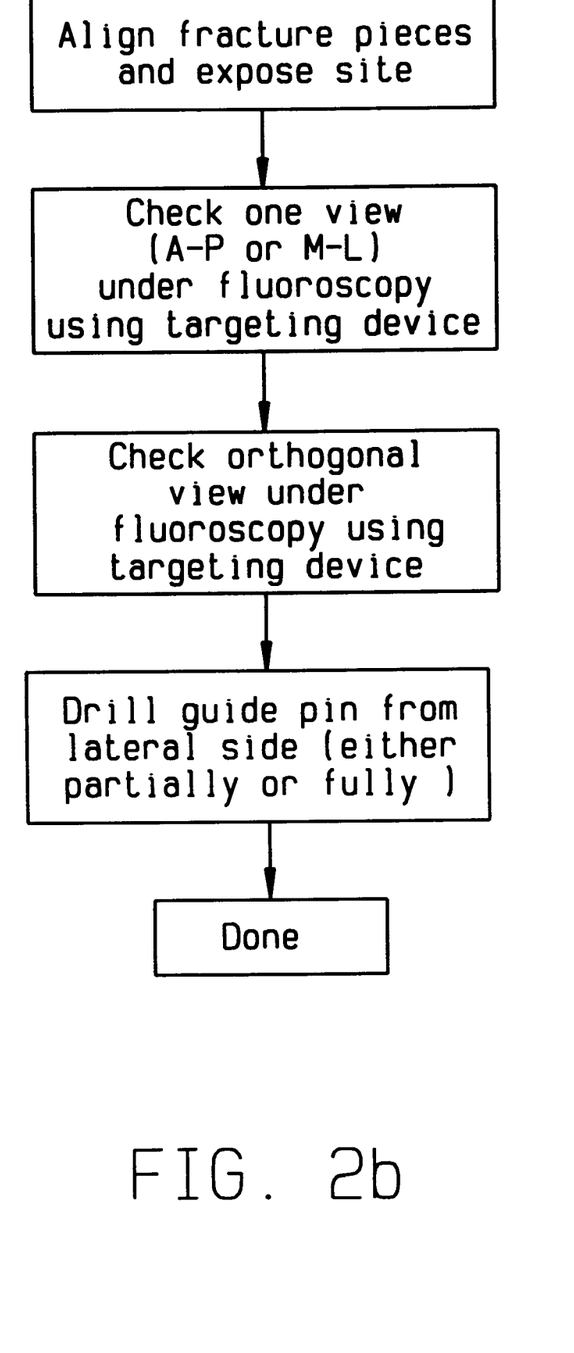
FIG. 2b is a flow chart depicting the process a surgeon uses to properly insert a guide-pin across a femoral neck fracture into the femoral head according to the present invention.

In one such surgical procedure, an incision is made through the skin of the hip to expose the femur starting at the tip of the greater trochanter. Using visual landmarks, the surgeon drills a guide-pin across the fracture into the femoral head. The surgeon checks the positioning of the guide-pin with an x-ray or fluoroscopic imaging device to determine if the positioning of the guide-pin is acceptable. If it is not, the surgeon must extract the guide-pin and reevaluate the insertion point and trajectory, then reinsert the guide-pin until its positioning is acceptable. When the guide-pin is in an acceptable position, a lag screw is advanced over the guide-pin into the femoral head to secure the bone for healing. A side plate is placed over the lag screw extender and secured to the lag screw and the femur for support and to compress the fracture. (See FIG. 2a).

Another means of securing a femoral neck fracture is with the use of an intramedullary locking nail. In that surgical procedure, an incision is made over the trochanteric region. The entry point is prepared using an awl. A guide wire is inserted into the femur and the intramedullary nail is inserted over the guide wire into the femur. A device is used to align a lag screw through a guide sleeve which is brought into contact with the femur. The screw is visually oriented and the surgeon drills a guide-pin across the fracture into the femoral head. The surgeon checks the positioning of the guide-pin with an x-ray or fluoroscopic imaging device to determine if the positioning of the guide-pin is acceptable. If it is not, the surgeon must extract the guide-pin and reevaluate the insertion point and trajectory, then reinsert the guide-pin until its positioning is acceptable. When the guide-pin is in an acceptable position, lag screw is advanced over the guide-pin, through an opening in the proximal portion of the intramedullary nail, and into the femoral head. The guide-pin is extracted and the intramedullary nail is secured by drilling screws through openings in the distal portion of the intramedullary nail.

Figure 1:
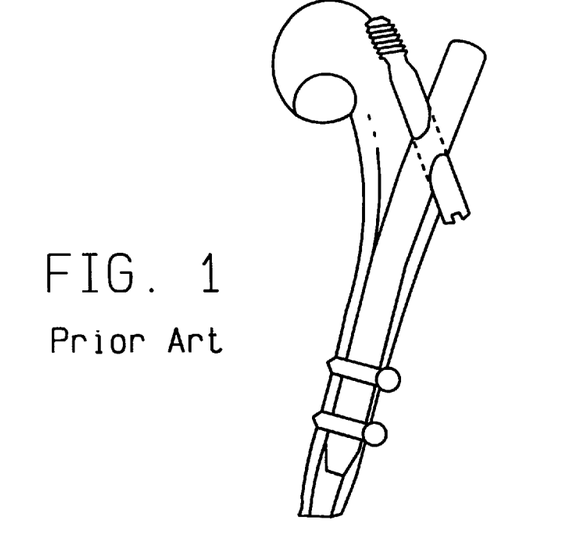
FIG. 1 is a side view of a intramedullary nail within a femur where the lag screw was not inserted properly.

An important part of both procedures is the placement of a compression or lag screw from the lateral side of the femur, through the femur, passing through the femoral neck, and into the femoral head. Inaccurate placement of the screw can lead to being misaligned with respect to the femoral head (see FIG. 1).

To avoid this, surgeons commonly spend a significant portion of their operating time iteratively inserting, checking, removing, and re-inserting a guide-pin over which the screw will be passed until accurate positioning within the femoral head is achieved.

Figure 3A:
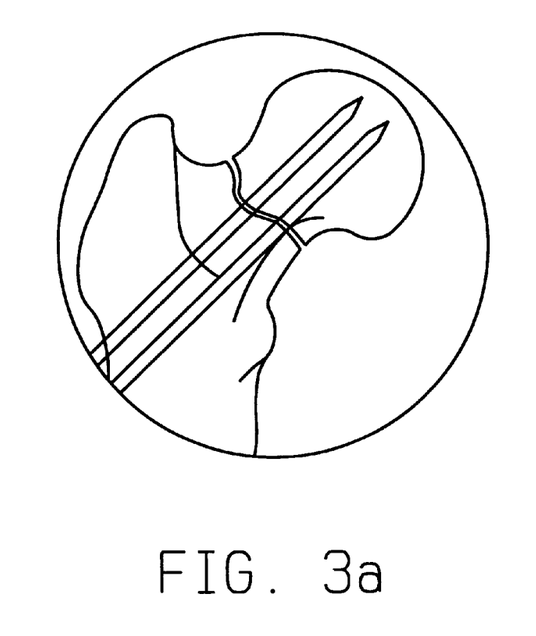
FIG. 3a is a perspective view of a fractured femur and femoral head from the anterior-posterior (AP) position.
Figure 3B:
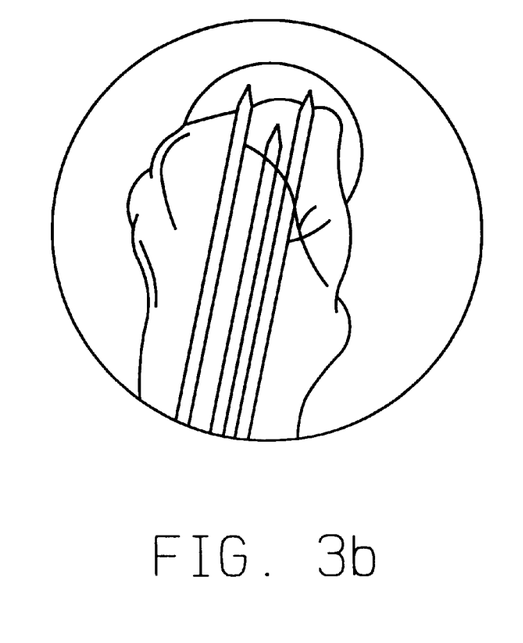
FIG. 3b is a perspective view of a fractured femur and femoral head from the medial-lateral (ML) position.

Surgeons typically use fluoroscopic image intensifiers to determine the accuracy of their guide-pin placement in two planes of view, the anterior-posterior ("AP") and the medial-lateral ("ML") (see FIGS. 3a & 3b). After satisfying themselves that the position of the guide-pin within the femur is accurate in one view, the fluoroscope is turned to the orthogonal view to check accuracy in that plane. If the wire or guide-pin is misplaced in the second view, the surgeon generally takes it out of the bone and reinserts it until satisfied with the position. By doing this, the surgeon loses reference of the initial view and must re-check the accuracy of the re-drilled guide-pin in both orthogonal views.

The surgeon repeats this process until reaching an acceptable position. This iteration takes time and results in greater x-ray exposure for patients and staff. Additionally, the process of inserting, removing, and reinserting the guide-pin could shred or seriously weaken the bone. The difficulty of guide-pin placement can also lead a frustrated surgeon to choose a less than optimal placement, putting the patient at risk for cut-out or faulty setting of the femoral head which could lead to settling of the femoral head.

U.S. Pat. No. 4,722,336 discloses a method and device to provide a three dimensional Cartesian coordinate of the target object using an x-ray or fluoroscopic imaging device and a radio-opaque targeting system. However, this method and device cannot be used where the fluoroscope cannot be aligned head-on with the guide piece and bony target.

U.S. Pat. No. 4,418,422 discloses an aiming device which is attached to an x-ray source. Similarly, this device cannot be used where a fluoroscope cannot be aligned head-on with the guide piece and the bony target. This device also cannot be used where the view-finder cannot be aligned head-on.

U.S. Pat. No. 4,976,713 discloses an aiming device that has a viewfinder with a radio-opaque component to align screws with anchoring holes in a centromedullar nail. This device also cannot be used where the viewfinder cannot be aligned head-on with the guide piece and bony target.

A similar limitation prevents the use in such circumstances of the device disclosed in U.S. Pat. No. 4,803,976 patent, which discloses the use of parallel radio-opaque fluoroscopy target markers aligned parallel but one beside, not above, the other target marker.

Presently, where a fluoroscope cannot be used aligned head-on with the guide piece and the bony target, surgeons have used visual landmarks and repeated insertion to obtain appropriate placement. This increases the surgeon's, the other medical personnel's, and the patient's exposure to x-ray radiation, increases the total operation time, and could lead to serious problems such as cut-out, as described above. There are currently no devices that are configured to be hand-held and easily used by the surgeon with an x-ray or fluoroscopic imaging device to accurately determine the proper entry point and trajectory for the insertion of an instrument, such as a pin, nail, screw, rod, wire, drill bit, or other implant. Also, there is currently no such targeting device which is adaptable and flexible to be used with different size patients which may require a targeting device to be custom adapted according to the patient's size and body shape to accurately project the proper alignment for the instrument or implant to repair the particular bony target.

There has therefore been a long felt need among surgeons and other medical personnel in this field for a targeting device which would allow the surgeon to align the guide-pin in both the AP and ML positions before actually inserting the guide-pin so that the guide-pin can be inserted accurately on the first attempt with a variety of sizes and shapes of patients, particularly, but not limited to, where an x-ray or fluoroscopic imaging device cannot be aligned head-on with the guide piece and the bony target.

SUMMARY OF THE INVENTION

The targeting device is generally configured to be a hand-held and operated orthopedic instrument which typically has a body and an arm member. The body of the device is generally comprised of two pieces, although some embodiments have a body that is one piece. Where the body of the targeting device is comprised of generally two pieces, one piece is an angle guide and the other is a guide piece. The angle guide is toward the front portion of the body of the targeting device and during use, the angle guide is in contact with bony tissue of the patient. Although other shapes could be used, the angle guide is typically shaped with a cylindrical back portion and an angular front portion, which contacts the bony tissue. When the body of the targeting device is pressed against bony tissue of the patient, the body of the targeting device becomes oriented at an angle to the bony tissue corresponding to the angle of the front portion of the angle guide. The angle guide has a passageway which may be substantially in the center of the angle guide and is large enough so that a particular instrument or implant can be passed through it.

The passageway of the angle guide corresponds to the passageway of the guide piece so that the particular instrument or implant can readily pass through the entire body of the targeting device. The guide piece and the angle guide may be connected in various ways, e.g., fixed or rotationally. A rotational connection allows the guide piece to rotate while the angle guide remains fixed in place, gripping bony tissue. With a rotational connection, the guide piece may rotate freely, by indexing, or with friction. Another benefit of the two piece body is that a custom angle guide may be used to properly align the instrument or implant by providing the proper angle to obtain the optimal orientation.

Extending from near the back end of the targeting device's body is an arm member. The purpose of the arm member is to extend outside the patient between the x-ray or fluoroscopic imaging device and the bony target. At some point on the arm member is at least one relatively radio-opaque target marker. The target marker is oriented between the x-ray or fluoroscopic imaging device and the bony target to indicate the placement of the instrument or implant when inserted into the bony target through the passageway of the body of the targeting device. For example, one embodiment has two relatively radio-opaque target markers which are parallel with one target marker aligned above the other such that when the two target markers overlap, the projected image is aligned to establish a plane that is co-planar with the targeting device's passageway.

The present invention is also a method of using a targeting device to predict an appropriate entry point and trajectory into bony tissue through which an instrument, such as a pin, screw, rod, nail, wire, drill bit, or other implant is inserted. By providing a targeting device to a surgeon or other user which is comprised of: a body with a passageway and an angular end capable of gripping bony tissue; and an arm member with at least one relatively radio-opaque target marker which may be imbedded within the arm member. The user can predict the placement of said instrument, such as a pin, screw, rod, nail, wire, drill bit, or other implant before drilling it into place with the use of an x-ray or fluoroscopic imaging device. By manipulating the device around the axis of the body of the targeting device, the surgeon can predict the placement of the instrument or implant from various fluoroscopic views without repeatedly placing and removing the instrument or implant itself. This method may dramatically reduce both operating and fluoroscopy time, saving time and reducing the exposure of surgeons and other medical personnel to x-ray radiation. These guides can be used with at least intramedullary interlocking nails and CHS implants and may be used in other surgeries requiring accurate implant or instrument placement relative to bony structures.

In a different embodiment, the present invention comprises a separate arm member which contains at least one relatively radio-opaque targeting member. Said relatively radio-opaque targeting member can be used to establish a plane that is co-planar with the base end of the arm member and indicates the projected placement of an implant or instrument, such as a pin, rod, nail, screw, or drill bit with the use an x-ray or fluoroscopic imaging device. Such arm member may be attached to or combined with another device to deliver the implant or instrument. In another embodiment, the present invention comprises a separate angle guide with a passageway which may be used to align the placement of an instrument, such as a nail, pin, screw, rod, wire, drill bit, or other implant. The angle guide has a front portion and a rear portion. One variation has a back portion which is cylindrical in shape, and a front portion that is angled relative to a bony surface to orient a passageway which extends through the angle guide. Said angle guide may be used with other instruments to further align the placement of the instrument or implant. Said angle guide comprises a plurality of teeth which may be cut in a variety of ways. One preferred embodiment has a cylindrical cut. Said teeth may be angled inward from the sides of said angle guide toward the center of the angle guide to further grip a contoured bony tissue body, such as a femur.

The present invention also includes a kit containing the various components described above.

BRIEF DESCRIPTION OF THE DRAWINGS

The above and other objects and advantages of the invention will be apparent upon consideration of the following detailed description taken in conjunction with the accompanying drawings in which like characters refer to like parts throughout and in which.

DETAILED DESCRIPTION OF THE PREFERRED EMBODIMENTS

Referring now to the drawings of the targeting device 10 of the present invention, targeting device 10 is comprised of several integrated components. These components are illustrated and described with regard to FIGS. 4a–4c, which show the completely assembled device, an alternate embodiment of the invention for use with intramedullary screws is shown in FIGS. 5a–5b.

Figure 4A:
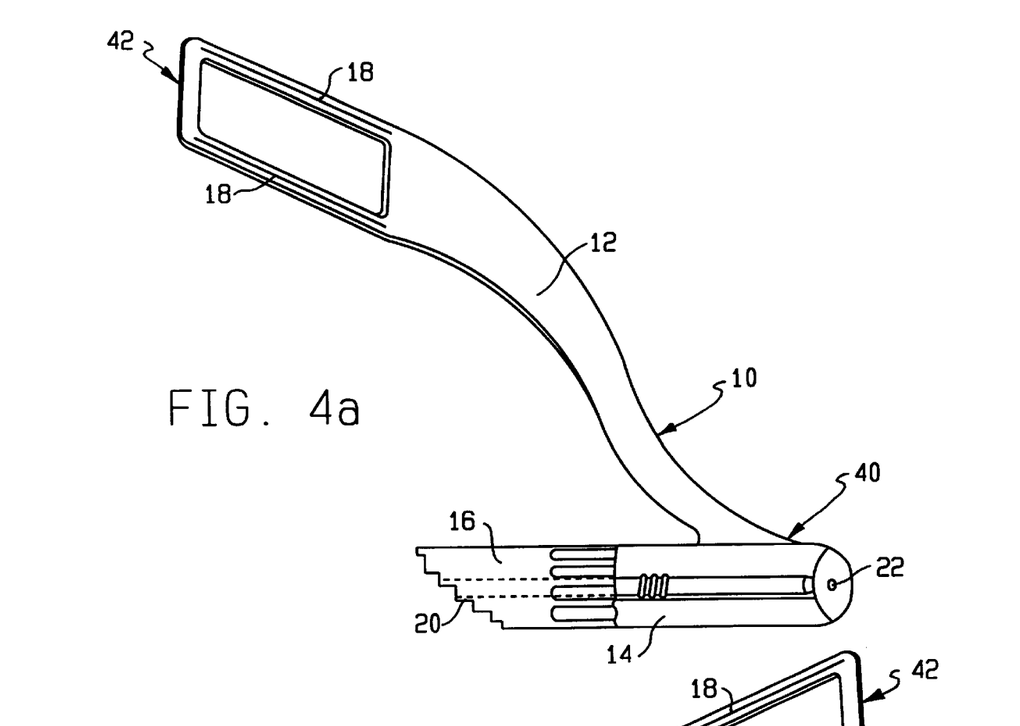
FIG. 4a is a perspective view of one preferred embodiment of the fully assembled targeting device for use with compression hip screws with a single arm member, two radio-opaque target markers, one style of angle guide; and a guide piece.
Figure 4B:
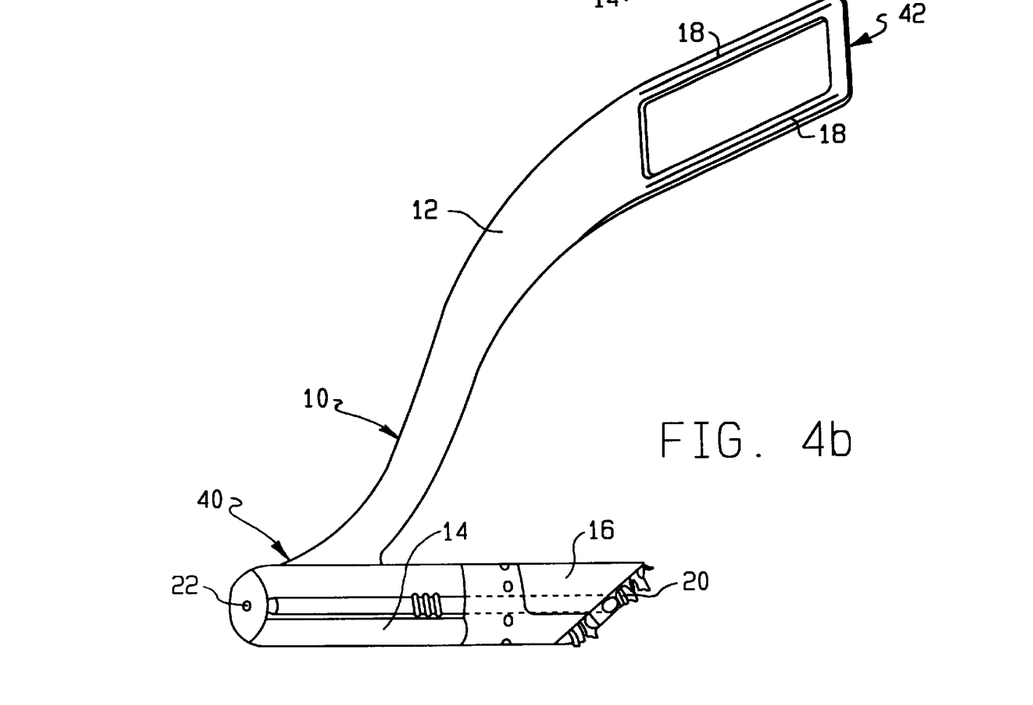
FIG. 4b is a perspective view of an alternate preferred embodiment of the fully assembled targeting device for use with compression hip screws with a different style angle guide.
Figure 4C:
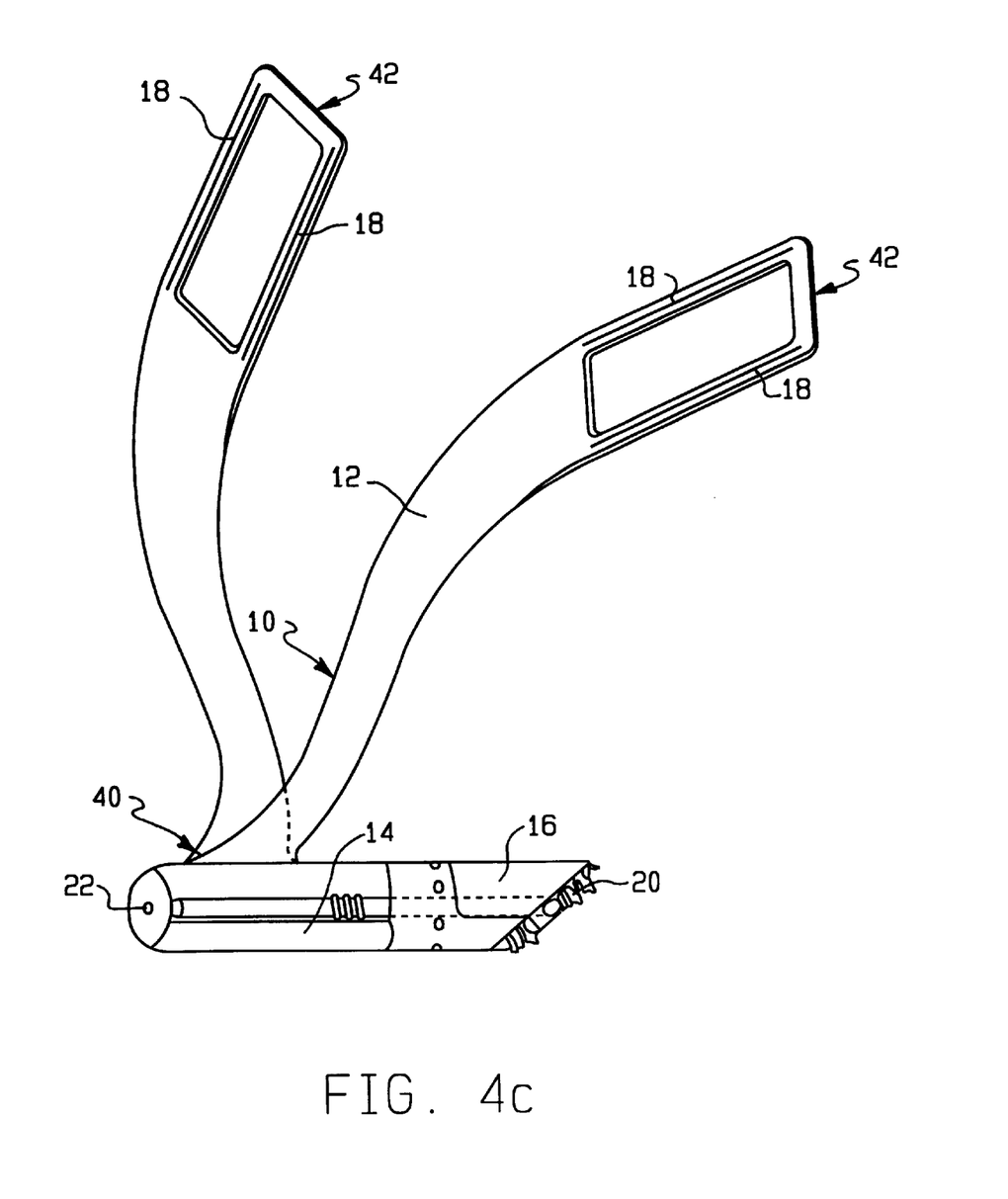
FIG. 4c is a perspective view of an alternate embodiment of the fully assembled targeting device for use with compression hip screws having two arm members, each with two radio-opaque target markers, the arm members being displaced from each other.
Figure 5A:
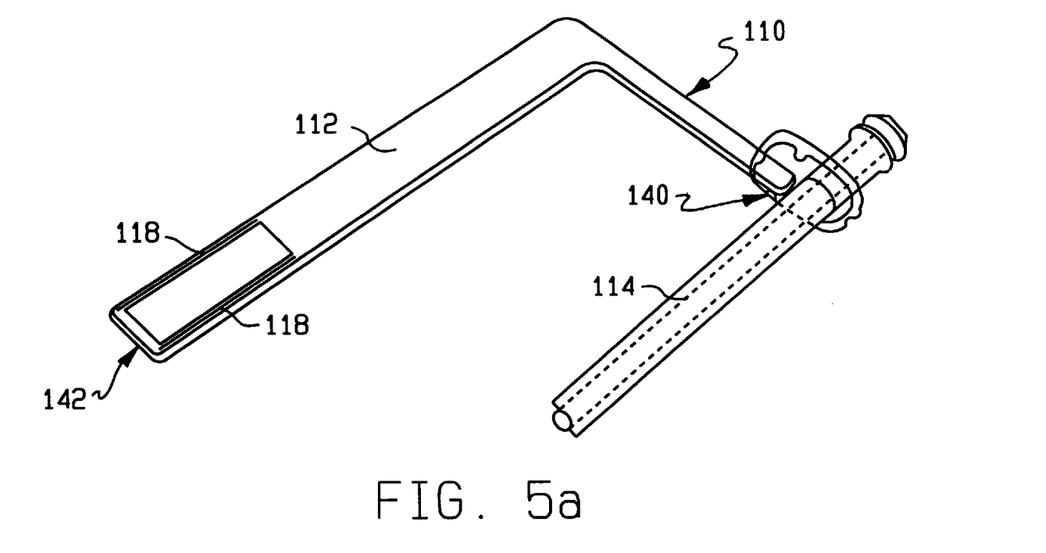
FIG. 5a is a perspective view of an alternate preferred embodiment of the fully assembled targeting device for use with intramedullary nails.
Figure 5B:
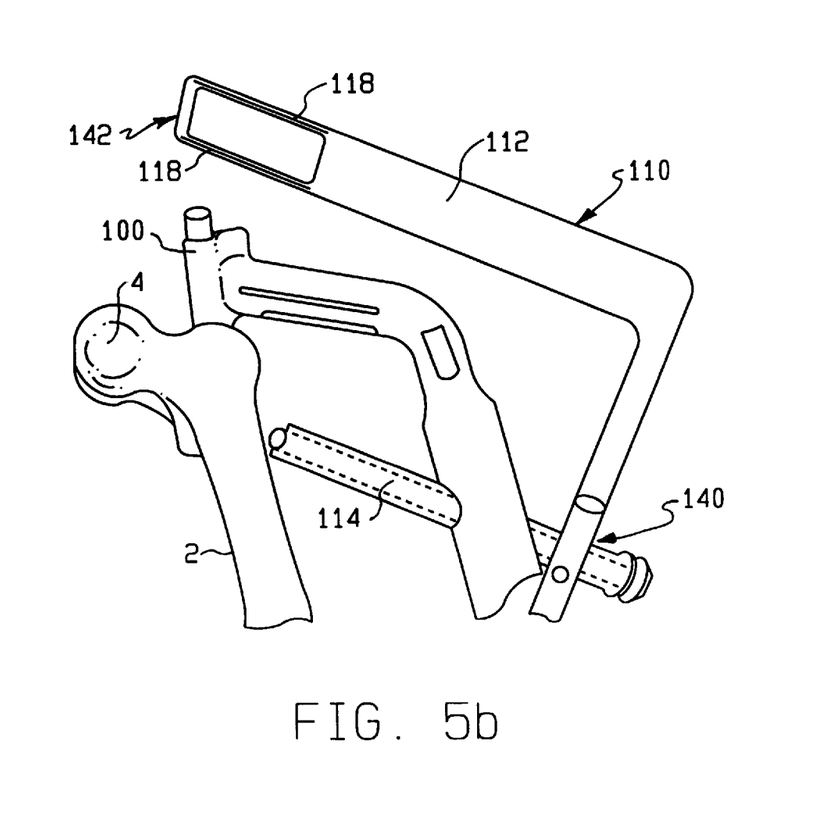
FIG. 5b is a perspective view of an alternate preferred embodiment of the fully assembled targeting device for use with intramedullary nails as oriented during use with proximal portion of a femoral bone.

Turning initially to FIGS. 4a–4c there is shown arm member 12 for targeting device 10. In a preferred embodiment arm member 12 is comprised of a plurality of separate elements which, upon being assembled as described below, form arm member 12 adapted for providing targeting for targeting device 10. The benefit of forming targeting device 10 from a plurality of separate, interconnected elements is that the dimensions of targeting device 10 may thereby be varied as necessary by substituting various sizes and variations of elements to conform to the size and shape of a particular area of a particular patient's body. In an alternate embodiment, however, it is further contemplated that targeting device 10 may be formed, e.g., molded, as a unitary construct containing only a single, or a limited number of structured elements.

In the preferred embodiment, targeting device 10 may be formed from, for example, various length arms 12, various sizes and shapes of angle guides 16, various styles of guide pieces 14, and various types of radio-opaque target markers 18. Arm member 12 may be preferably formed from Raydel™ but may also use alternate materials, i.e., other than Raydel™, including plastics, glasses (e.g., fiberglass), metals and even wood, as long as such materials are capable of supporting targeting device 10. Arm member 12 can be different lengths to accommodate targeting for different sizes of femurs 2 or other bony tissue and can either be fixed to guide piece 14 or may be removable so that difference lengths or styles can be interchanged. Arm member 12 extends from base 40 to end 42. The preferred embodiment of arm member 12 has a rectangular section removed proximal end 42 of arm member 12 creating a rectangular gap at the end 42 of arm member 12. The removal of this rectangular section makes the relatively radio-opaque target markers 18 show more distinct by x-ray or fluoroscopic imaging device. This portion may be small or could extend the length of arm member 12. The gap may also be various other shapes so as to allow an enhanced view of the relatively radio-opaque target marker 18. Similarly, target markers 18 may be small or could extend the entire length of arm member 12. An alternative embodiment of arm member 12 comprises only the two target markers 18 essentially extending from guide piece 14. Another embodiment of targeting device 10 includes two or more arms 12 displaced from each other. (See FIG. 4c). Where targeting device 10 has two arms displaced from each other, e.g. by 90° so that one arm member 12 is in the AP position while the other arm member 12 is simultaneously in the ML position. (See FIG. 4c).

Angle guides 16 are preferably formed from some metal such as stainless steel or aluminum, however, the material used to form this component is only limited in that it should be a material that is hard enough to grip the bone tissue and to maintain its passageway, for example, various plastics could be used. Angle guides 16 can vary by the type and the cut of teeth 20 that are used. For example, a preferred embodiment of angle guide 16 has a small number, of inwardly angled, cylindrically cut teeth 20 to grip femur 2 when using targeting device 10. Alternatively, angle guide 16 could have more teeth and a different cut. Angle guide 16 can be made with many different angles and is easily interchangeable so that the targeting device 10 can be custom fit to the particular femur 2.

Another embodiment includes a quick release connection to facilitate the exchange of angle guides 16. Angle guide 16 is connected to guide piece 14. Guide piece 14 is preferably made of the same material as arm member 12. Guide passageway 22 aligns and extends through both guide piece 14 and angle guide 16 and can be of varying sizes to accommodate different size pins, screws, nails, wires, or drill bits. Another embodiment of angle guide 16 contains a recessed pin that the surgeon can extend with a button or switch to secure angle guide 16 to femur 2 for increased stability. A further embodiment of angle guide 16 is secured to the femur 2 through the use of a vacuum, clamp or strap. Another embodiment of angle guide 16 contains an opening to drill a screw or pin through to secure angle guide 16 to femur 2. Another embodiment employs a simple clamping device which secures angle guide 16 to femur 2.

The relationship between the guide piece 14 and arm member 12 can be fixed or rotational. A preferred embodiment has a guide piece 14 which rotates at least from the AP orientation to the ML orientation, rotating arm member 12 accordingly, while the angle guide 16 remains fixed on femur 2. Another embodiment has a guide piece 14 with an indexing rotation which may correlate to a particular number of degrees of rotation relative to the angle guide 16 which remains fixed on femur 2. Another embodiment may have a friction fit between guide piece 14 and angle guide 16, to prevent arm member 12 from freely swinging without a minimal amount of force. Yet another embodiment has a guide piece 14 with a variable friction setting to increase and decrease the friction resistance when rotating the guide piece 14 relative to the fixed angle guide 16. Another embodiment of guide piece 14 has a lock-out feature so that when target markers 18 of arm member 12 are aligned in the AP position, the lock-out feature can be enacted and the guide piece 14 will turn to the ML position and stop or lock in that position.

Figure 4D:
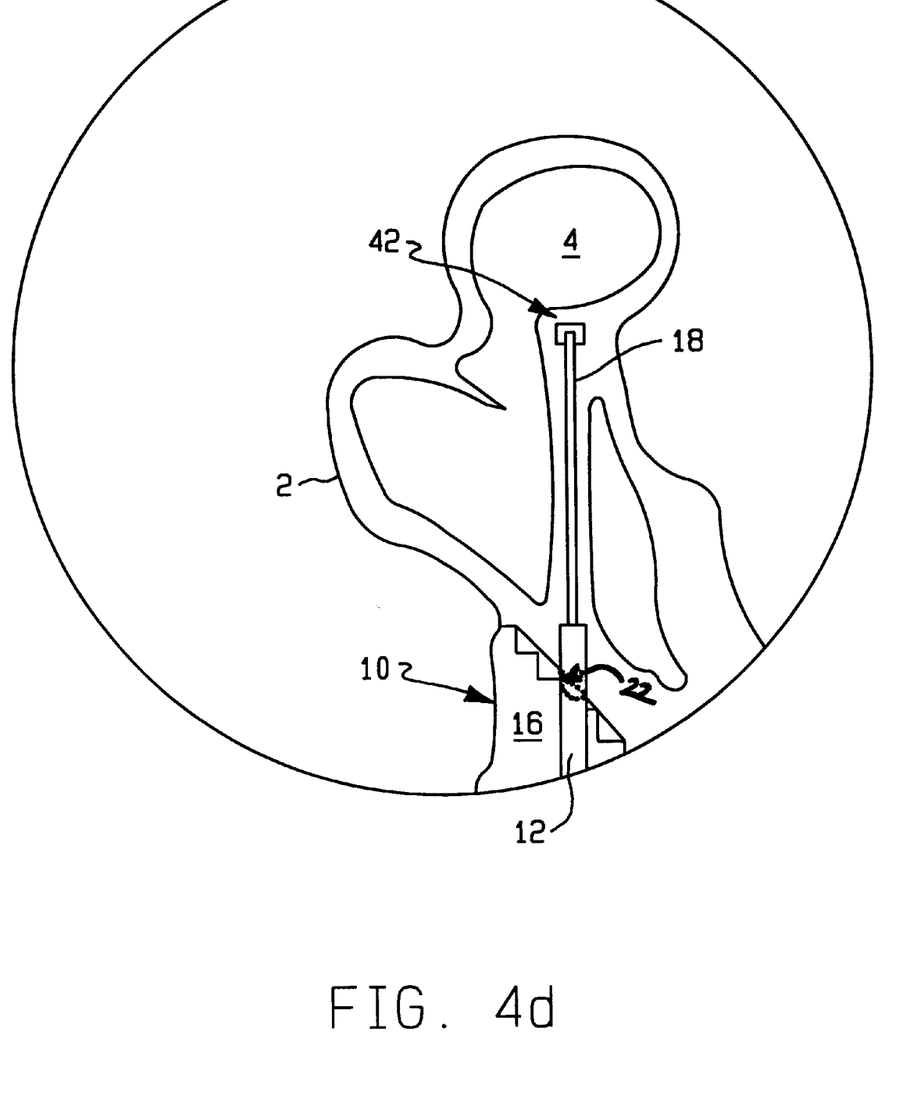
FIG. 4d is a perspective view of a simulated fluoroscopic image from the AP perspective and with the radio-opaque target markers aligned.

FIG. 4d shows a fluoroscopic image of targeting device 10 from the AP perspective over femur 2 and, in particular, femoral head 4. Radio-opaque target markers 18 are aligned so that only first marker 18 appears with second marker 18 co-planar to first marker 18. These aligned target markers 18 are then co-planar with a beam from an x-ray or fluoroscopic imaging device and a desired location or trajectory relative to a bony target, such as femoral head 4. These aligned target markers 18 are also co-planar with passageway 22. The superimposed position of aligned target markers 18 indicates where the guide-pin will insert into femoral head 4 through passageway 22. In addition to this view, a surgeon will also align target markers 18 in the ML position to ensure that the guide-pin will insert into the middle of femoral head 4. This is done by turning or rotating arm member 12 orthogonally from the AP position to the ML orientation and moving the x-ray or fluoroscopic imaging device so that it is also oriented in the ML position. Arm member 12 is then moved until target markers 18 overlap and appear as one marker 18. When target markers 18 overlap, the positioning of the superimposed target markers 18 indicates the position of the guide-pin if inserted into the femoral head 4. A surgeon may easily align target markers 18 in the AP position and then the ML position and have a certainty that the guide-pin will be in the appropriate position in the femoral head 4 without having to iteratively remove and reinsert the guide-pin until satisfactory positioning is achieved. Radio-opaque target markers 18 may be made from any relatively radio-opaque material. In a preferred embodiment, stainless steel wires are used as target markers 18. Other embodiments may use tantalum, gold, or other high atomic number metals. Alternatively, a contrast coating such as barium sulfate may be used to coat portions of arm member 12 to substitute for or to enhance target markers 18. Other possible radio-opaque materials will be obvious to one skilled in the art. Target markers 18 may be of various shapes and configurations so that when aligned co-planar with passageway 22, target markers 18 provide some indication of alignment. Target marker 18 may be substantially one dimensional, such as a wire, substantially two dimensional such as a triangle, or three dimensional. Examples of such target markers 18 include: two wires which overlap when co-planar with passageway 22; two sets of wire segments which appear separate with gaps between segments when not co-planar with passageway 22, however, appear as one solid line when co-planar with passageway; two wires, one of which is larger than the other to indicate the direction to rotate arm member 12 to be co-planar with passageway 22; one two dimensional target marker 18, e.g. triangular, circular, trapezoidal, which appears one dimensional when co-planar with passageway 22.

FIGS. 5a and 5b pertain to an embodiment of the present invention that can be used with an intramedullary nail. The device 110 is comprised of several components. Component 100 in FIG. 5b is a standard intramedullary alignment device which is well known in the art and is described in U.S. Pat. No. 5,334,192 to Behrens. This alignment device attaches to the intramedullary nail to assist in determining the proper point and trajectory of insertion. Device 110 fits onto component 100 to allow the alignment of the lag screw after the intramedullary nail is inserted into femur 2. This is done similarly to targeting device 10 where the surgeon orients device 110 in the AP position so that markers 118 align. The x-ray or fluoroscopic imaging device is moved to the ML position and arm 112 is also moved so that markers 118 align. This will orient the guide-pin so that it may be inserted through guide 114, through the proximal opening on the intramedullary nail and into femoral head 4. The components of device 110 may be varied similarly to that of the corresponding components of targeting device 10.

In a preferred embodiment, arm 112 is attached to guide 114 for rotation therewith by a standard spring clip 140. Arm 112 can then be rotated from the AP plane to the ML plane by rotating guide 114.

Another object of the present invention is to provide a method of aligning an orthopedic instrument or implant with bony tissue using an x-ray or fluoroscopic imaging device. This is done by providing a passageway 22 through guide piece 14 and angle guide 16, through which the instrument implant such as a pin, screw, nail, wire, or drill bit is passed, and further providing at least one targeting device, such as arm member 12, fixed to said guide piece 14 and containing at least one relatively radio-opaque target marker 18 that establishes a plane that is co-planar with an axis of said passageway 22. The targeting device is then manipulated until the plane established by the targeting device is co-planar with a beam from an x-ray imaging device and a desired location or trajectory relative to a bony target in at least one view and passing said instrument or implant through said guide passageway 22. In another method, said targeting device rotates about the passageway 22 axis.

Figure 6A:
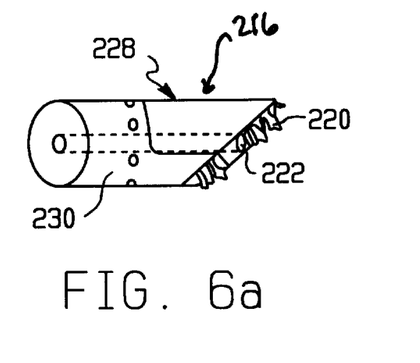
FIG. 6a is a perspective view of a preferred embodiment of an angle guide which can be used to position a targeting device to a bone to prevent unintentional movement of the device while allowing for intentional movement of the device.
Figure 6B:
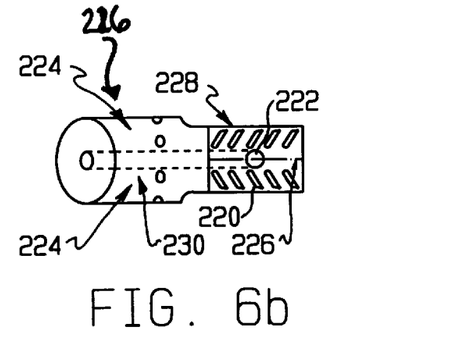
FIG. 6b is a different perspective view of the preferred embodiment of an angle guide which can be used to position a targeting device to a bone to prevent unintentional movement of the device while allowing for intentional movement of the device.
Figures 6C, 7:
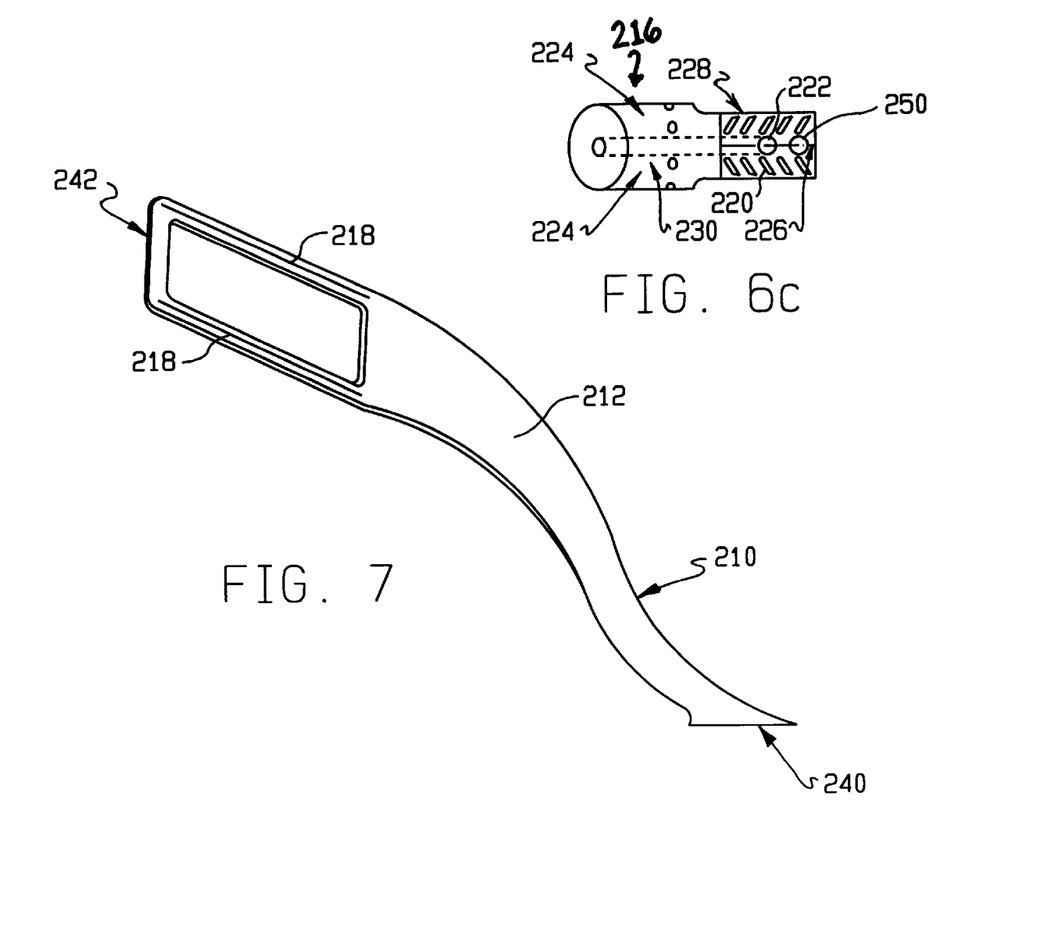
FIG. 6c is a perspective view of another preferred embodiment of an angle guide which can be used to position a targeting device to a bone and which includes an opening through which a means to secure the angle guide to the bony tissue can be inserted.
FIG. 7 is a perspective view of an arm member with two radio-opaque target markers which can be used in determining an appropriate entry point and trajectory for an instrument or implant, such as a pin, rod, screw, nail, wire, or drill bit.

FIGS. 6a–6c show another embodiment of the present invention which is angle guide 216 which can be used to assist in the positioning of the insertion of an instrument, such as a nail, pin, rod, screw, wire, drill bit, or other implant into a bony target. Angle guide 216 may have a plurality of teeth 220 which are attached along the front portion of angle guide 216. Teeth 220 may be a cylindrical cut or other cut to allow for angle guide 216 to grip the bony surface without unintentional movement or sliding of angle guide 216. At the same time, teeth 220 allow the user to intentionally move or adjust the position of angle guide 216 to achieve the best alignment. FIG. 6c shows an embodiment of angle guide 216 with opening 250 through which an attachment means may be inserted to further secure the angle guide 216 to a bony surface. The attachment means may be a vacuum tube, a securing pin, or a screw. Alternatively, a simple strap or clamp may also be used to secure angle guide 216. This means of securing the angle guide 216 would further guard against incidental movement of the targeting device. Such movement may require the removal of the vacuum, strap or clamp securing angle guide 216 or the retraction of a securing pin or screw. Teeth 220 may extend straight across the front face of angle guide 216 or may angle inwardly or even outwardly. A preferred embodiment angles teeth 220 in from each side 224 of angle guide 216 to center line 226. Angle guide 216 may be formed with the front portion 228 extending toward the back portion 230 along sides 224 at any angle from 0° to 90°. Also, the angle may be fixed or variable from front portion 228 to back portion 230.

FIG. 7 shows another embodiment of the present invention which is an arm 212 which can be used to assist a surgeon or other medical personnel with the determination of the proper insertion point for an instrument or implant, such as a nail, pin, rod, screw, or drill bit. Arm 212 may be fixed or attached in some manner to a device at base 240 or used alone in some manner. Arm 212 may have a rectangular piece cut from arm 212 which is relatively small or relatively large proximal end 242. Arm 212 may be comprised of a small body made of Raydel™, or some substitute material as described above, with long or short target markers 218 which extend from the body of arm 212. Target markers 218 may be some relatively radio-opaque material such as stainless steel, tantalum, or a high atomic number metal. Alternatively, target markers 218 may be some contrast, such as but not limited to barium sulfate, painted or otherwise interposed on arm 212.

The present invention also includes a kit which may contain all components or a variety of the components mentioned above. One skilled in the art will appreciate that the present invention can be practiced by other than the described embodiments, which are presented for the purpose of illustration only and not of limitation. The present invention is therefore only limited by the following appended claims.

All references cited herein are hereby incorporated by reference.

We claim:

1. An orthopedic targeting device for the placement of an instrument in a desired position relative to a bony target using an imaging device, said device comprising:

a body of said targeting device defining a guide passageway through which said instrument is passed; and more than one arm member fixed to said body, each arm member containing at least one relatively radio-opaque target marker that establishes a plane that is coplanar with an axis of said passageway.

2. The device of claim 1 wherein said targeting device has two arm members disposed from each other approximately 90° apart about said axis.

3. An orthopedic targeting device for the placement of an instrument in a desired position relative to a bony target using an imaging device, said device comprising:

a body of said targeting device defining a guide passageway through which said instrument is passed; and at least one targeting member fixed to said body wherein said targeting device has two relatively radio-opaque target markers extending at least partially from one end of said targeting member toward the opposite end of said targeting member; and a substantially open gap in the targeting member between each of said target markers wherein said target markers establish a plane that is coplanar with an axis of said passageway.

4. An orthopedic targeting device for the placement of an instrument in a desired position relative to a bony target using an imaging device, said device comprising:

a body of said targeting device defining a guide passageway through which said instrument is passed; and at least one targeting member fixed to said body and containing at least one relatively radio-opaque target marker that establishes a plane that is coplanar with an axis of said passageway wherein said targeting device has at least one area of said targeting member coated with a contrast medium.

5. An orthopedic targeting device for the placement of an instrument in a desired position relative to a bony target using an imaging device, said device comprising:

a body of said targeting device defining a guide passageway through which said instrument is passed; and at least one targeting member fixed to said body and containing at least one relatively radio-opaque target marker that establishes a plane that is coplanar with an axis of said passageway;

wherein said targeting device has an angle guide with a front angled portion and a rear portion comprising at least part of said body of said targeting device and configured and dimensioned to be secured to bony surface; and wherein said angle guide has teeth which are broader at the base of said teeth than at the apex of said teeth and are on said front angled portion of the angle guide.

6. An orthopedic targeting device for the placement of an instrument in a desired position relative to a bony target using an imaging device, said device comprising:

a body of said targeting device defining a guide passageway through which said instrument is passed; and at least one targeting member fixed to said body and containing at least one relatively radio-opaque target marker that establishes a plane that is coplanar with an axis of said passageway wherein at least one relatively radio-opaque target marker has at least two substantially perpendicular sections;

at least one first section extending distally from a point proximal one end of said targeting member toward the opposite end; and at least one second section substantially perpendicular to the first section and extending toward a bony target.

* * * * *